United States Patent [19]

Knollmueller

[11] 4,207,247

[45] Jun. 10, 1980

[54] PREPARATION OF TRIALKOXYSILANOLS

[75] Inventor: Karl O. Knollmueller, Hamden, Conn.

[73] Assignee: Olin Corporation, New Haven, Conn.

[21] Appl. No.: 44,829

[22] Filed: Jun. 1, 1979

[51] Int. Cl.² .................................................. C07F 7/04
[52] U.S. Cl. ...................................... 556/463; 556/458
[58] Field of Search ................................ 260/448.8 A

[56] References Cited

U.S. PATENT DOCUMENTS

| | | | |
|---|---|---|---|
| 2,727,054 | 12/1955 | Wright | 260/448.8 A |
| 2,758,127 | 8/1956 | Goldschmidt et al. | 260/448.8 A |
| 3,965,135 | 6/1976 | Knollmueller | 260/448.8 A |
| 3,965,136 | 6/1976 | Knollmueller | 260/448.8 A |
| 4,077,993 | 3/1978 | Knollmueller | 260/448.8 A X |

*Primary Examiner*—Paul F. Shaver
*Attorney, Agent, or Firm*—William A. Simons; Thomas P. O'Day

[57] ABSTRACT

An improved method is disclosed for the preparation of trialkoxysilanols. The process involves hydrolysis of corresponding trialkoxyhalosilanes, conducted using a two-phase system in the presence of catalytic amounts of select phase transfer agents.

10 Claims, No Drawings

PREPARATION OF TRIALKOXYSILANOLS

Silicate esters, long appreciated as a class of compounds, only recently have been extensively investigated and recognized as exhibiting physical properties which indicate superior potential utility as synthetic lubricants and functional fluids. One major obstacle for such application, however, has been their hydrolytic instability.

Novel silicate ester compounds now have been developed which overcome the drawback of hydrolytic instability, and, in turn, continue to feature highly favorable physical properties. Such novel compounds, characterized as alkoxysilane cluster compounds, and their preparation are described in the present inventor's commonly assigned U.S. Pat. Nos. 3,965,136, 3,992,429 and 4,058,546, the disclosures of which are hereby incorporated by reference in their entireties.

The synthesis of each of the respective alkoxysilane cluster compounds involves the use of sterically hindered trialkoxysilanols as starting materials. These trialkoxysilanols have the general formula:

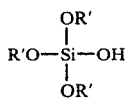

wherein R' is independently selected from hydrogen, alkyl, alkenyl, aryl, or aralkyl, with the proviso that at least a majority of the pendant R' groups attached to the central Si atom are sterically hindered alkyl groups having at least 3 carbon atoms. It is desirable that R' be selected from hydrogen, alkyl or alkenyl having from about 1 to about 18 carbon atoms or aryl or aralkyl having about 6 to about 24 carbon atoms, preferably, R' is selected from hydrogen, alkyl or alkenyl having about 1 to about 8 carbon atoms, or aryl or aralkyl having about 6 to about 14 carbon atoms, subject to the preceding proviso. The majority of the R' groups are sterically hindered alkyl groups having about 3 to about 24 carbon atoms; preferably the majority of the R' groups are sterically hindered alkyl groups having about 4 to about 12 carbon atoms. In the most preferred embodiment, all of the R' groups are sterically hindered alkyl groups. The term "sterically hindered alkyl groups" is meant to be defined as alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly preferred sterically hindered alkyl groups include sec. butyl, iso-butyl, 2-ethyl butyl, 2-ethyl pentyl, 3-ethyl pentyl, 2-ethyl hexyl, 3-ethyl hexyl, 2,4-dimethyl-3-pentyl, etc. Sec. butyl groups are most preferred.

Silanols generally are prepared by a hydrolysis reaction from their corresponding chlorosilanes in the presence of a base compound. The base may be any compound which will accept hydrogen halide and thereby promote the formation of the silanol compounds pursuant to Equation (A) shown below:

$$R_3Si-Cl + H_2O + B \rightarrow R_3Si-OH + B \cdot HCl \quad (A)$$

wherein, for example, R is an alkyl group and B is the base compound.

Due to their instability, however, silanols, including trialkoxysilanols, generally are difficult to prepare and isolate, and often require specially adapted techniques for each type of respective silanol product. For example, trialkoxysilanols having primary lower alkyl groups tend to form condensation products. The silanol self-condenses to form disiloxand with the elimination of water, $$2(R'O)_3Si-OH \rightarrow (R'O)_3Si-O-Si(OR')_3 + H_2O, \quad (B)$$

and also condenses with unreacted halosilane starting material, $$(R'O)_3Si-OH + Cl-Si(OR')_3 + B \rightarrow B \cdot HCl + (R'O)_3Si-O-Si(OR')_3. \quad (C)$$

Such side reactions lower yields and may even make independent existence of the silanol nearly impossible.

The trialkoxysilanols which are the subject of the presently invented process contain sterically hindered alkyl groups, as defined above, which significantly enhance silanol stability. According to U.S. Pat. No. 2,727,054, these silanols, represented by tri-sec-butoxysilanol, can be prepared by first converting a trialkoxyhalosilane to an amide through reaction with ammonia, and then hydrolyzing the amide to the corresponding silanol. These reactions can be outlined as follows:

$$(R'O)_3Si-Cl + 2NH_3 \xrightarrow{heptane} NH_4Cl + (R'O)_3Si-NH_2 \quad (D)$$

$$(R'O)_3Si-NH_2 + H_2O \xrightarrow{heptane} NH_3 + (R'O)_3Si-OH. \quad (E)$$

While this reaction scheme is reasonably productive, it is beset by the drawbacks that condensation products, such as disiloxanes, lower yields, and some amide survives the hydrolysis to contaminate the product silanol.

A favorable synthesis procedure to prepare sterically hindered trialkoxysilanol compounds has been discovered which involves the reaction of a trialkoxyhalosilane with solid bicarbonate, preferably, NaHCO$_3$, in the presence of a critical catalytic amount of water, as represented by the following equation:

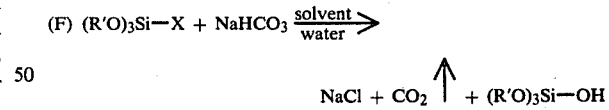

wherein X is a halogen, preferably chlorine, and R' is defined as above. Such a reaction has been found to offer excellent yields; and, the purity of the product silanol compound further accommodates storage stability. As Equation (F) suggests, the reaction preferably is carried out in a solvent. While the solvent is not strictly necessary, it does serve to moderate the rate of reaction and thereby to enhance the separation of the unreacted NaHCO$_3$ and by-product NaCl from the trialkoxysilanol compound product. This discovered process is the subject of a copending patent application of the present inventor, Attorney's Docket No. C-7741. The disclosure of this application hereby is incorporated by reference in its entirety.

Now, in a further improvement, it has been discovered, according to the present invention, that hydrolysis of trialkoxyhalosilanes to sterically hindered trialkoxysilanols, as defined above, can be accomplished using a novel, two-phase system. This system employs a nonprotonic solvent as the organic phase and an aqueous slurry or solution of an inorganic base as the aqueous phase. Also, in order to initiate the hydrolysis reaction and minimize any side reactions, it is critical to add to the reaction mixture catalytic amounts of select phase transfer agents. The mechanism of the two-phase simultaneous reactions can be illustrated by the following equations:

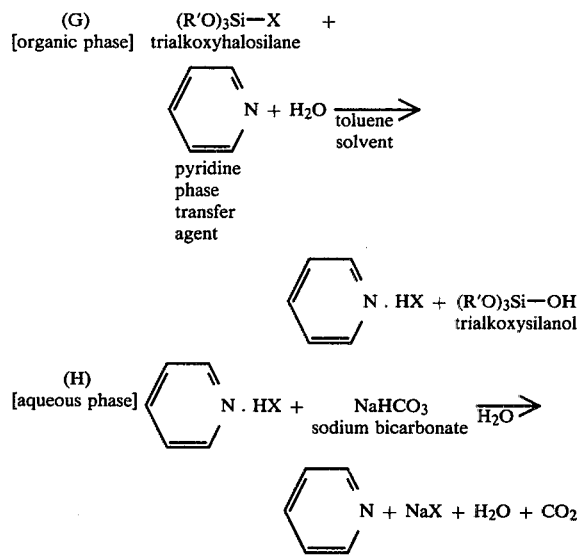

wherein X and R' are defined as above. The phase transfer agent, (e.g., pyridine) which is preferentially soluble in the organic phase, reacts with the halosilane to form the silanol as well as the hydrohalide salt, which is preferentially soluble in the aqueous phase. In the aqueous phase, the hydrohalide salt reacts with the inorganic base and once again is freed for return to and reaction in the organic phase.

The organic phase of the system consists of a nonprotonic solvent. Among the solvents which may be used are benzene, toluene, xylene, hexane, heptane, high boiling petroleum ether, other water insoluble ethers, and the like. Toluene is particularly preferred. The volume of the solvent generally ranges from about 300 ml to about 1500 ml per mole of trialkoxyhalosilane starting material. Preferably, the volume of solvent ranges from about 600 to about 800 ml per mole of trialkoxyhalosilane.

The aqueous phase is an aqueous slurry or solution of an inorganic base. Included in the inorganic bases that may be employed are NaOH, NaHCO$_3$, Na$_2$CO$_3$, and the like. Sodium bicarbonate, NaHCO$_3$, and mixtures thereof with sodium hydroxide, NaOH, are preferred. Generally, the minimum amount of base used is about one mole per mole of trialkoxyhalosilane; preferably a slight excess is used, about 1.1 to about 1.3 moles of base per mole of the trialkoxyhalosilane. The volume of aqueous phase during reaction generally ranges from about 200 to about 400 ml of water per mole of trialkoxyhalosilane.

Catalytic transfer agents are selected from weak tertiary organic bases that are soluble in both the aqueous phase as well as the organic phase. Such transfer agents include nitrogen-containing tertiary organic bases such as pyridine and triethylamine, as well as quaternary ammonium salts represented by the formula R$_4$N$^-$X$^-$ (wherein R represents a C$_4$ to C$_{12}$ hydrocarbon radical and X represents a halogen, preferably chlorine). Pyridine is the preferred transfer agent, since it is also employed in the intended subsequent use of the subject trialkoxysilanols in the synthesis of alkoxysilane cluster compounds. The phase transfer agent generally is used in an amount ranging from about 0.01 to about 0.1 mole per mole of trialkoxyhalosilane. The preferred range is about 0.04 to about 0.06 mole of transfer agent.

Reaction temperatures may range from as low as about 0° to about 110° C. It is generally preferred to operate in a range of about 20° to about 30° C. Preferably, the trialkoxyhalosilane reactant is added gradually over a period ranging from about 0.5 to about 16.0 hours. An addition time of about 4.0 to about 6.0 hours has been found particularly preferable.

After the reaction of the trialkoxyhalosilane with the aqueous organic base has proceeded to completion, the aqueous NaCl and slight excess of NaHCO$_3$ and/or NaOH base is phased out of the reactor. The organic silanol solution then can be dried by azeotropic distillation of the toluene organic solvent and aqueous residues. The distillation may be conducted at atmospheric pressures or under reduced pressure.

The trialkoxysilanols have particular utility as reactants in the preparation of alkoxysilane cluster compounds. A practical advantage offered by this two-phase system is the ready adaptability of the system to in-situ alkoxysilane cluster production. In specific, rather than isolating the pure silanol, it is preferred to strip off the residual water and the solvent only to a limited extent so that the silanol product is recovered in solution with solvent at a concentration best suited for subsequent utility in alkoxysilane cluster synthesis. The optimum solvent concentrations for preparation of alkoxysilane clusters are more fully described in the present inventor's U.S. Pat. No. 4,077,993, the disclosure of which hereby is incorporated in its entirety by reference.

Using this preferred reaction scheme, to prepare such cluster compounds, one needs only to add an acceptor base, such as pyridine, and a trihalosilane to the prepared trialkoxysilanol/toluene solution. The entire operation, including both silanol and cluster compound synthesis can conveniently be accomplished in a single reactor vessel. A typical alkoxysilane cluster synthesis can be represented by the following equation:

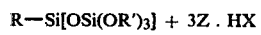

wherein X represents halogen groups; R is hydrogen, an alkyl, alkenyl, aryl or aralkyl; each R' is independently selected from the same group as R with the proviso that at least a majority of R' radicals are sterically hindered alkyl groups having at least 3 carbon atoms; and Z is a hydrogen halide acceptor base.

The following examples depict various embodiments of the present invention; they are intended to be illustrative rather than limiting in nature. All parts and percentages are by weight unless otherwise specified.

PREPARATION OF TRI-SEC-BUTOXYSILANOL

EXAMPLE I

A one-liter three-necked flask was equipped with a stirrer, reflux condenser and an equilibrated dropping funnel. The outlet of the reflux condenser was connected to a flow meter to monitor gas evolution. The flask was charged with 250 ml toluene, 42 g $NaHCO_3$ (0.5 mole) and 200 ml water. To this slurry was added at room temperature, dropwise 95.1 g (sec. $C_4H_9O)_3SiCl$, 99.2% purity (principal impurity (sec. $C_4H_9O)_4$-Si)=0.336 mole. No $CO_2$ evolution was seen when the addition was started. Introduction of 1.2 ml (~0.015 mole) pyridine started the $CO_2$ evolution. The $CO_2$ evolved at ~180 ml/min. while the chlorosilane was added over a 40-minute period. After a post reaction time of one hour, the aqueous phase was withdrawn and the undissolved $NaHCO_3$ washed out with four 100–200 ml water washes. The organic phase was dried with 50 g $MgSO_4$, filtered and vacuum stripped. 81.2 g (sec. $C_4H_9O)_3SiOH$ obtained, having 96.37% purity by VPC, represents a 91.3% yield based on chlorosilane charged.

EXAMPLE II

The experiment I was repeated, but 0.5 g tetra-n-butoxyammonium chloride was used instead of the pyridine.

The $CO_2$ evolution was slower and the addition time was two hours. 81 g silanol with 94% purity was obtained, giving a yield of 85.66%.

EXAMPLE III

Into a two-liter three-necked flask, equipped with a stirrer and a dropping funnel was placed 97.2 g sodium carbonate (0.917 mole) 390 ml water, 614 ml pyridine catalyst and 624 ml toluene. The $Na_2CO_3$ is 129.4% of theory required for the 400.8 g chlorosilane to be reacted. Through the dropping funnel, 400.8 g ClSi(OC$_4$H$_9$)$_3$ (1.417 moles) was dropped into the vigorously stirred mixture during 138 minutes. After the addition was completed, stirring was continued for 1½ hours to finish the reaction. For ease of work up, 624 ml toluene was added, followed by 200 ml water. The aqueous phase was separated from the organic phase in a separatory funnel. After four washes with about 100 ml water each, the wash was chloride free. The reaction mixture was dried by azeotropically distilling of water residuals and toluene. This azeotroping was done at 210–240 mm pressure, adjusted such that the pot temperature did not exceed 80° C. The residual toluene was vacuum stripped at ~60° C./12 mm Hg; last traces of solvent were removed by pumping overnight at 25°–30° C./0.1 mm Hg. 364.1 g crude silanol was recovered, with a purity of 93.05% (by VPC). The materials recovery, based on the chlorosilane charged, was 95.4% while the yield was 90.2% silanol.

EXAMPLE IV

Using equipment and techniques described in Example III, 792.6 g ClSi(OC$_4$H$_9$)$_3$ (2.802 moles) was dropped into a mixture of 194.8 g $Na_2CO_3$ (1.838 moles) 780 ml water, 1248 ml toluene and 12.8 ml pyridine during 5.5 hours. The reaction gave 761.2 g crude silanol of 93.35% purity. Based on chlorosilane charged, the materials recovery was essentially quantitative and the yield of silanol, HOSi(OC$_4$H$_9$ sec.)$_3$, was 95.9%.

EXAMPLE V

A three-necked one-liter flask was equipped with a stirrer, a thermometer, and two equilibrated dropping funnels. The flask was charged with 500 ml toluene, 4.18 g pyridine (0.052 mole), 8.75 g $NaHCO_3$ (0.104 mole) and 218 ml water. A few drops of phenolphthalein pH indicator also was added.

To the slurry in the flask was added 312 g (sec. $C_4H_9O)SiCl$ (1.1029 moles) over a 35-minute period. During this same time, aqueous NaOH (44.12 g dissolved in 200 ml water) was added from the other dropping funnel at a rate to maintain the color of the indicator at just pink. At the end of both simultaneous additions, a few drops of NaOH was added to keep the solution pink (pH ~9.1).

After 15 minutes of stirring, the phases were allowed to separate. A pH check showed a pH of about 10+ indicating a slight excess of NaOH. The pH was adjusted back down to 8 with acetic acid, and then the mixture was stirred for a 1-hour post reaction period.

The phases were separated and the organic phase was washed four times with 200 ml water, after which the wash was chloride free.

The wet organic phase was azeotroped at 200 mm Hg at a pot temperature not exceeding 75° C. The last traces of toluene were stripped at 48° C. and 10 mm Hg on a rotary evaporator. 298 g of crude silanol was recovered. The materials recovery, based on the chlorosilane charged, was 96.7%, while the yield was 92.26% silanol.

EXAMPLE VI

Into a flask, equipped with a stirrer and thermometer, was charged 156 ml toluene, 100 ml ClSi(OC$_4$H$_9$ sec.)$_3$ (d=0.946=96.4 g 0.334 mole) 1.6 ml pyridine and 20 ml water.

While keeping the temperature at 23°–25°, 0.334 mole NaOH (as 100 ml containing 133.8 g NaOH/l) was dropped in during 40 minutes. After a post reaction period of one hour and the usual work up, there was recovered 84.4 g product having a purity of 88.7%.

Based on ClSi(OC H$_9$ sec.)$_3$ charged, the materials recovery was 95.4% and the yield 87.6%.

EXAMPLE VII

This example demonstrates the azeotroping at reduced pressure and simulates delays encountered in large scale operations. A 12-liter three-necked flask was equipped as described in Example I. It was charged with 3275 ml toluene, 19 ml pyridine (~0.235 mole), 539 g $NaHCO_3$ (6.416 moles) and one liter water. To this slurry was added, over a six-hour period, 1394 g (sec. $C_4H_9O)_3SiCl$, 99.8% purity (=4918 moles). Fifteen minutes after the addition was completed, the $CO_2$ evolution ceased. After a post reaction time of one hour, one more liter of water was added to dissolve most unreacted $NaHCO_3$ (excess). This solution was syphoned off.

To simulate a delay in washing, one liter water was added and after stirring for 10 minutes, the phases were allowed to separate. The organic phase was left standing 12 hours in contact with the aqueous phase. No sludge formation was seen. The organic phase was washed three times with one liter water; after the last wash, the water was Cl$^-$ free.

The organic phase was transferred to a six-liter distillation flask. The entrained residual water and toluene was distilled off at pressures manually adjusted from 250 mm Hg to ~20 mm during the distillation leaving the pot temperature at all times at 80° C.

Last traces of toluene were vacuum stripped at ~1 mm. 1273 g silanol (sec. C$_4$H$_9$O)$_3$SiOH with a purity of 93.79% was obtained, which is 4.515 moles silanol or 91.8% yield based on chlorosilane charged.

Newly formed by-products were identified as (R'O)$_3$SiOSi(OR')$_3$ and (R'O)$_3$SiOSi(OR')$_2$OH (R'=sec. C$_4$H$_9$ by) mass spectroscopy.

EXAMPLE VIII

This example demonstrates the stability of the silanol as well as the insensitivity of the process towards a interruption. Using equipment described in Example I, a mixture of 670 ml toluene, 110 g NaHCO$_3$ (1.309 moles) 200 ml water and 4 ml pyridine (~0.049 mole) was reacted within four hours with 90% of a mixture of 283 g (sec. C$_4$H$_9$O)$_3$SiCl (99.66% purity=0.997 mole) in 375 ml toluene.

The addition was interrupted, but the stirring was continued on overnight. Then the remainder of the chlorosilane was added and two hours allowed for a post reaction time.

After four washes with 200 ml portions of water each, the wash was Cl⁻ free. A VPC, at this point, showed silanol to be 94.5% pure (solvent free basis). The crude mixture contained 1046 ml toluene, 740 ml of which was distilled off at atmospheric pressure. The distillation time was five hours. During this time, the pot temperature rose from 114° to 124° C. The toluene removed in this fashion represents the maximum one would take off to arrive at a optimum solvent level for alkoxysilane cluster synthesis. The remainder of the toluene was vacuum stripped to determine yields.

258.3 g product was obtained, which contained 94.55% (sec. C$_4$H$_9$O)$_3$SiOH (by VPC). This represents a yield of 0.924 mole or 92.63% based on Cl—Si(OC$_4$H$_9$sec.)$_3$ charged.

PREPARATION OF SEC-BUTOXYSILANE CLUSTER

EXAMPLE IX

This experiment demonstrates the suitability of silanol, made by phase transfer techniques, for cluster synthesis. 2100 g HO—Si(OC$_4$H$_9$sec.)$_3$ from various phase-transfer preparations, (average purity 94.45%, 7.5 moles) 831 g pyridine (10.5 moles) and 1600 ml toluene were reacted with 373.7 g CH$_3$SiCl$_3$ (2.5 moles) in 400 ml toluene.

Reaction conditions and work up was as described in U.S. Pat. No. 4,077,993. 2772.2 g crude cluster silane was obtained, containing 77.26% cluster (80.54% yield based on silanol or 73.9% based on ClSi(OC$_4$H$_9$)$_3$.

After distillative work-up, 1595 g cluster CH$_3$—Si[OSi(OC$_4$H$_9$sec.)$_3$]$_3$ was obtained, which is 76.56 yield based on silanol or 69% based on chlorosilane starting materials (averaged).

EXAMPLE X

The apparatus described in Example I was used. Silanol was prepared from a mixture of 681 ml toluene, 112 g NaHCO$_3$ (1.33 moles) 200 ml water, 4 ml pyridine catalyst and 290.3 g (sec. C$_4$H$_9$O)$_3$SiCl (1.026 moles) in accordance with the procedures outlined in Examples I, II, VII, and VIII.

The wet toluene solution was azeotroped at 80° C. pot temperature adjusting the pressure. 477 ml toluene and residual water was thus removed. Analysis by VPC showed that the purity of silanol was 94% and 0.965 mole silanol were in solution.

It was cooled to −8°, mixed with 109.1 g pyridine (1.379 moles). To the stirred mixture was added 48.06 g CH$_3$SiCl$_3$ (0.321 mole) in 50 ml toluene. During the addition, the temperature was allowed to rise to +7. After the addition, which took 2.5 hours, the reaction mixture was post reacted for three hours at 80°. After this 30 ml sec.-butanol was added to convert by-product H$_3$C—Si[OSi(OC$_4$H$_9$)$_3$]$_2$Cl to the alkoxy ester. Pyridine hydrochloride was washed out in four washes with 200 ml water each. Toluene was then removed with residual water by atmospheric distillation, last traces were vacuum stripped.

254.8 g crude product afforded 189.1 g cluster or 0.227 mole, which is 66.37% yield based on (C$_4$H$_9$O)$_3$SiCl charged.

What is claimed is:

1. In a process for the preparation of sterically hindered trialkoxysilanol compounds of the formula:

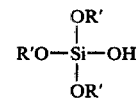

wherein R' is independently selected from hydrogen, alkyl, alkenyl, aryl, or aralkyl, with the proviso that at least a majority of the pendant R' groups attached to the central Si atom are sterically hindered alkyl groups having at least 3 carbon atoms,
    by hydrolyzing a corresponding trialkoxyhalosilane of the formula, (R'O)$_3$Si-X, wherein X is a halogen and R' is defined as above, the improvement comprising reacting the trialkoxyhalosilane in the presence of a catalytic amount of a phase transfer agent, and,
    conducting the hydrolysis in a two-phase system comprising an organic phase consisting of a nonprotonic solvent and an aqueous phase containing an inorganic base.

2. The process of claim 1 wherein said phase transfer agent is a tertiary organic base soluble in both the organic and aqueous phases.

3. The process of claim 2 wherein said phase transfer agent is selected from the group consisting of nitrogen-containing tertiary organic bases and quaternary ammonium salts.

4. The process of claim 3 wherein said phase transfer agent is selected from the group consisting of pyridine, triethylamine and quaternary ammonium salts of the formula, R$_4$N$^+$X$^-$, wherein R is a C$_4$ to C$_{12}$ hydrocarbon radical and X is a halogen.

5. The process of claim 4 wherein said phase transfer agent is pyridine.

6. The process of claim 1 wherein the aqueous phase contains an inorganic base selected from the group consisting of NaOH, Na$_2$CO$_3$, NaHCO$_3$, and mixtures thereof.

7. The process of claim 6 wherein the inorganic base is selected from the group consisting of NaHCO$_3$, and mixtures thereof with NaOH.

8. The process of claim 1 wherein the organic phase is a non-protonic solvent selected from the group consisting of benzene, toluene, xylene, hexane, heptane, high boiling petroleum ether, other water insoluble ethers, and mixtures thereof.

9. The process of claim 8 wherein the organic phase is toluene.

10. The process of claim 1 wherein tributoxychlorosilane is hydrolyzed in the presence of a catalytic amount of pyridine, using a two-phase system comprising a toluene organic phase and an aqueous phase containing an inorganic base selected from the group consisting of $NaHCO_3$ and mixtures of $NaHCO_3$ with NaOH.

* * * * *